United States Patent [19]
Griffith

[11] Patent Number: 5,400,789
[45] Date of Patent: * Mar. 28, 1995

[54] SHEATH FOR GUIDE WIRE PROBE

[76] Inventor: James M. Griffith, 15251 S. 26th St., Phoenix, Ariz. 85044

[*] Notice: The portion of the term of this patent subsequent to Apr. 13, 2010 has been disclaimed.

[21] Appl. No.: 225,606

[22] Filed: Apr. 11, 1994

Related U.S. Application Data

[63] Continuation of Ser. No. 18,058, Feb. 16, 1993, Pat. No. 5,327,885, which is a continuation-in-part of Ser. No. 773,037, Oct. 8, 1991, Pat. No. 5,201,315, and a continuation-in-part of Ser. No. 11,335, Jan. 29, 1993, Pat. No. 5,249,580.

[51] Int. Cl.6 .............................................. A61B 8/12
[52] U.S. Cl. ................................ 128/662.06; 128/772
[58] Field of Search ....................... 128/662.03, 662.06, 128/772, 4; 601/2; 604/280

[56] References Cited

U.S. PATENT DOCUMENTS

| | | | |
|---|---|---|---|
| 4,762,129 | 8/1988 | Bonzel | 128/344 |
| 4,794,931 | 1/1989 | Yock | 128/660.03 |
| 4,815,470 | 3/1989 | Curtis et al. | 128/662.03 |
| 4,889,128 | 12/1989 | Millar | 128/662.06 |
| 4,899,757 | 2/1990 | Pope, Jr. et al. | 128/662.06 |
| 4,917,097 | 4/1990 | Proudian et al. | 128/662.06 |
| 4,951,677 | 8/1990 | Crowley et al. | 128/662.06 |
| 5,000,185 | 3/1991 | Yock | 128/662.03 |
| 5,024,234 | 6/1991 | Leary et al. | 128/663.01 |
| 5,046,503 | 9/1991 | Schneiderman | 128/692 |
| 5,090,958 | 2/1992 | Sahota | 604/98 |
| 5,178,150 | 1/1993 | Silverstein et al. | 128/662.06 |
| 5,179,961 | 1/1993 | Littleford et al. | 128/772 |
| 5,201,315 | 4/1993 | Griffith | 128/662.06 |
| 5,203,338 | 4/1993 | Jang | 128/662.06 |
| 5,209,730 | 5/1993 | Sullivan | 128/772 |
| 5,220,924 | 6/1993 | Frazin | 128/662.06 |
| 5,246,009 | 9/1993 | Adams | 128/772 |
| 5,249,580 | 10/1993 | Griffith | 128/662.06 |

OTHER PUBLICATIONS

Brochure "Get The Inside View", InterTherapy.
Brochure, "Proformer Guiding Catheters—New Products for AHA 1992", Mansfield Boston Scientific Corporation.

Primary Examiner—George Manuel
Attorney, Agent, or Firm—Woodcock Washburn Kurtz Mackiewicz & Norris

[57] ABSTRACT

A catheter for delivering both a probe and a balloon to a lumen in a subject. The probe is most preferably an ultrasonic imaging probe and the balloon a dilation balloon. The catheter comprises, at a proximal end, a triple lumen section that comprises a guidewire lumen, a probe lumen and a lumen for communicating with a balloon. As the lumens run toward the distal end of the catheter, a transition section is provided that merges the probe lumen and the guidewire lumen into a single lumen. The single lumen continues distally and is surrounded by the balloon. Distal of the balloon, the single lumen defines an imaging window section. The catheter terminates in a distal tip that is preferably tapered along both its inner and outer diameters; the tip comprises a distal lumen sized to accept a guidewire. In certain preferred embodiments, radio opaque markers are used to delineate the various sections of the catheter. Among its many advantages, the present invention readily permits back loading of a guidewire.

6 Claims, 3 Drawing Sheets

FIG. 6

SHEATH FOR GUIDE WIRE PROBE

CROSS-REFERENCE TO RELATED APPLICATIONS

This is a continuation of application Ser. No. 08/018,058, filed Feb. 16, 1993, now U.S. Pat. No. 5,327,885, which is a continuation-in-part of application Ser. No. 07/773,037, filed Oct. 8, 1991, now issued U.S. Pat. No. 5,201,315, issued on Apr. 13, 1993, and application Ser. No. 08/011,335, filed Jan. 29, 1993, now issued U.S. Pat. No. 5,249,580, issued on Oct. 5, 1993, a division thereof.

The present invention relates to invasive therapeutic and diagnostic devices, such as intravascular ultrasound imaging devices and balloon dilation catheters. More particularly, improved catheters and methods for their use are disclosed that place imaging and dilation functions into a single catheter. The present invention therefore allows reduced cost and catheterization time when compared with using separate catheters for the two functions.

BACKGROUND OF THE INVENTION

Dilation catheters without ultrasound capability are well known and accepted. For example, angioplasty for coronary and leg arteries is common. Various companies market dilation catheters, including: SciMed Life Systems, Minneapolis, Minn.; Advanced Cardiovascular Systems, Santa Clara, Calif.; and USCI, Billerica, Mass.

Catheters for ultrasound imaging, especially for imaging coronary artery geometry, are also well known and are marketed by several companies including: Diasonics, Milpitas, CA; Cardiovascular Imaging Systems, Sunnyvale, Calif.; Endosonics, Pleasanton, Calif.

The benefits of a single catheter providing both dilation and ultrasound imaging, rather than two separate catheters, include decreased cost and catheterization time. Decreasing catheterization time allows a given catheterization facility and staff to serve more patients; among other benefits, this fact will likely decrease the patient's cost. Also, certain patients find catheterization somewhat frightening and uncomfortable. Presumably, they would prefer a faster procedure.

The potential for a combined dilation/imaging catheter has been recognized, for example, in U.S. Pat. No. 4,951,677—Crawley, et. al., describing a catheter sheath with a dilation balloon mounted over an ultrasound transducer so that an area can be imaged while it is opened with the balloon. This device, however, has certain limitations. It is not adapted for use with the steerable guidewires that physicians routinely use to guide catheters or other invasive devices into a desired arterial branch or other location. In addition, the disclosed catheter requires imaging through both the sheath and the balloon materials. As will be appreciated by those of skill in the art, this limits image quality because it is difficult to entirely rid a balloon of air bubbles. Since the bubbles are strong acoustic reflectors, they degrade image quality. Also, each layer of material between the ultrasound transducer and the artery creates opportunities for signal attenuation, which decreases sensitivity, and for acoustic reverberations, which introduce imaging artifacts. Finally, the disclosed catheter is of a larger diameter than is necessary for imaging with a given probe because the transducer is covered by both the sheath and the balloon, rather than just the sheath.

A catheter disclosed in U.S. Pat. No. 4,841,977—Griffith et al. shows a type of transducer array with a covering dilation balloon. The disclosed device is not, however, well suited to imaging when the balloon is deflated. In addition, the described system produces poor quality two-dimensional ultrasound images because of the limited number of different ultrasound data lines available to form each image.

U.S. Pat. No. 4,917,097—Proudian, et. al. describes a dilation/imaging catheter in which a large number of transducers, e.g., sixty-four, are arranged in an array and interfaced to special purpose integrated circuits mounted beside the transducer array at the distal end of the catheter. The balloon is slightly proximal of the array. The arrangement uses a steerable guidewire for catheter placement but exhibits a number of significant limitations. For example, the ultrasound transducers, circuits, and signal processing hardware incorporated into the catheter are substantially more complex than the corresponding elements of a mechanically scanned (rotating) system. In addition, the catheter slides along in contact with the artery (or other lumen) wall whenever the ultrasound imaging plane is moved, thereby failing to minimize trauma.

Thus, it can be seen that there is a long recognized, yet unfulfilled need for a catheter design which incorporates both a dilation balloon and an ultrasound imaging probe which, for reasons of simplicity and cost, is preferably mechanically rotated. Moreover, it would be desirable to provide such a catheter that is manipulated into place with a steerable guidewire for ease and speed of use. It would also be desirable to provide such a catheter design that minimizes cross-sectional area so as to be useable in small lesions, arteries or lumens. It is therefore an object of this invention to provide a catheter apparatus for combined balloon dilation and ultrasonic imaging. Another object of the present invention is to provide a dilation/imaging catheter of small cross-section in its distal length. A further object of the invention is to provide a single lumen/dual lumen transition in a catheter that facilitates passing the guidewire from the single lumen and into a specified lumen of the dual lumen section of catheter. Another object of the present invention is to provide methods of using catheters. An additional object of the present invention is to provide a method of backloading a guidewire from a single lumen section of a catheter and into a chosen lumen of a dual lumen section.

SUMMARY OF THE INVENTION

These and other objects are attained, for example, by one preferred embodiment of the present invention that provides a flexible catheter for positioning a dilation balloon and an ultrasound transducer within a selected region of a patient lumen. The catheter comprises a distal tip section with a tip lumen adapted to accept a guidewire, a single lumen, imaging-window section connecting proximally to the distal tip section, a dilation section connecting proximally to the imaging-window section and a triple lumen section extending proximally from the dilation section.

The dilation section comprises a balloon with a length of flexible tubing (defining the balloon lumen) passing through the balloon, and a second tube entering the proximal end of a balloon for inflation and deflation. The distal end of the balloon sealingly attaches to the length of tubing. The proximal end of the balloon sealingly attaches around both the length of flexible tubing and second tube.

The triple lumen section comprises a guidewire lumen adapted to accept a guidewire, a probe lumen adapted to accept an ultrasound probe, and an inflate/deflate lumen, defined by the second tube, for operating the dilation balloon. The guidewire and probe lumens come together as a single lumen in a transition proximal of the balloon and connect with the balloon lumen.

The probe lumen, balloon lumen, and imaging section lumen are sized and connected such that the tip of an ultrasound probe may be inserted into the proximal end of the probe lumen, slide through the probe lumen, through the balloon lumen and into the lumen of the imaging window section.

The guidewire lumen, balloon lumen, imaging window lumen, and distal tip lumen are sized and connected such that a guidewire can be passed through them.

Most preferably, the catheter of the present invention includes a tapered flexible distal tip which has a tip lumen for accepting a guidewire; the tip also preferably contains a radio opaque marker for X-ray viewing. Similarly, one or more radio opaque markers are placed near or within the balloon section for X-ray visualization. Additionally, in certain embodiments of the present invention, a "quad" lumen section comprising a fourth lumen is provided in place of the triple lumen section.

The present invention also discloses methods of imaging and dilating a patient lumen by using apparatus substantially made in accordance with the above-described invention, an ultrasound probe, and a guidewire. The guidewire is advanced through the subject until the distal tip of the wire is distal to the region to be imaged and dilated; the catheter is then advanced over the wire until the imaging window section has passed into the region to be imaged. The wire is then withdrawn from the single lumen portion of the catheter while holding the catheter stationary (in the distal or proximal directions) within the subject and leaving the distal tip of the wire within the guidewire lumen. The ultrasound probe tip is next advanced into the imaging window section while holding the catheter stationary within the patient lumen, and the probe is activated to obtain ultrasound images. The probe tip is then retracted into the probe lumen, the guidewire tip pushed distal of the catheter tip. The catheter is advanced over the wire (while the guidewire tip remains distal of catheter tip) until the balloon is within the region to be dilated. The balloon is inflated and/or deflated in accordance with standard procedures. Next, the catheter is moved proximally so that the imaging window section is across the now dilated area and the wire tip is retracted into the wire lumen, wherein either the catheter or the guidewire is moved first. The probe is then advanced (moved distally) into the imaging window section and images obtained by activating the probe. Finally, the catheter, probe and guidewire are withdrawn from the patient.

The preceding described an image-before-dilate, dilate, image-after-dilate sequence. It is understood, however, that the invention is not limited to this one sequence. For example, if image-after-dilate revealed the need, one could perform a second dilation by simply repeating the required steps. In addition, it will sometimes be desirable to omit portions of the sequence. For example, imaging may show that dilation is unnecessary and hence the dilation is omitted. For these reasons, the descriptions of the invention set forth herein are not to be construed as limiting the invention, and reference should be made to the claims to determine the true scope of the present invention.

BRIEF DESCRIPTION OF THE DRAWINGS

These and other objects and features of the present invention will appear after careful consideration of the preceding and following descriptions, including reference to the drawings in which.

DETAILED DESCRIPTION OF THE PREFERRED EMBODIMENTS

Figure 1:
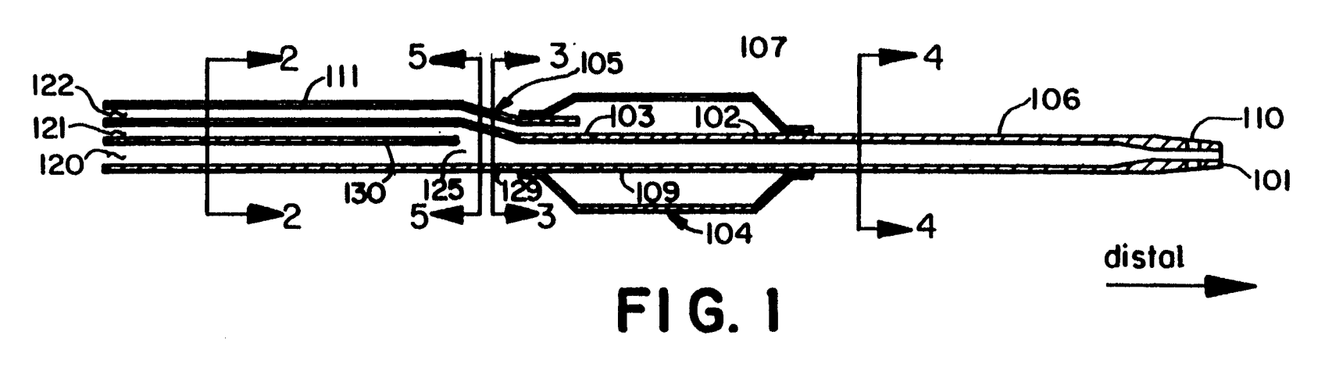
FIG. 1 is a longitudinal cross-section of the distal end of a catheter made in accordance with the present invention.

Referring now to FIG. 1, a distal portion of a catheter 100 made in accordance with the present invention is illustrated. Those of ordinary skill will understand that catheter 100 is substantially tubular and flexible, and that FIG. 1 shows a longitudinal cross-section of the catheter. Those of ordinary skill will also be familiar with the types of materials and methods used to build such catheters. Preferably, the catheter 100 of the present invention is lubricated on its exterior surface and the interior lumen surfaces may also be coated with lubrication. Assuming a coronary artery application, the complete catheter is preferably about 1.0 to 1.5 meters long. The distal tip 101 of the catheter 100 is preferably about 1.0 cm long and flexible so that it may be advanced over a guidewire (not shown) that has been threaded through a coronary artery or other patient lumen. The distal tip 101 of catheter 100 is also preferably soft and tapered so that it is atraumatic to the artery or lumen wall. The inside diameter of the distal tip 101 is preferably also tapered as shown in FIG. 1; this taper permits a guidewire to smoothly move distally through the distal tip 101, which is preferably radio opaque or contains an opaque marker 110, as shown, to indicate the catheter tip location in X-ray views. The tapered inside diameter of the distal tip 101 is preferably sized to slidingly accept a guidewire and is most preferably between about 10 to 20 mils (0.010–0.020 inches) in diameter for coronary imaging applications.

The imaging window section 106 of the catheter 100 connects proximally with the distal tip 101 and is a flexible, elongated, substantially tubular section that is also substantially transparent to the acoustic energy used for imaging. The diameter of the lumen of the imaging window section 106 is sized to pass either a guidewire or an ultrasound imaging probe. The outside diameter of the imaging window section 106 is most preferably a few thousandths of an inch larger than the inside diameter. A wide range of choices exist for selecting the length of this portion of catheter 100. A relatively long imaging window section 106 having a length of about 10 cm (3.9 inches), allows collecting images over a long length of the patient lumen in which the catheter 100 is placed by moving the probe longitudinally without repositioning the catheter 100. For example, a relatively long imaging window section 106 is useful for searching for a suspected stenosis or in three-dimensional imaging. On the other hand, a relatively short imaging window section 106, of about 2.0 cm (0.8 inches), allows a dilation with much less catheter positioned distal of the stenosis. Thus, for example, in a percutaneous transluminal coronary angioplasty (PTCA) procedure a short window may be appropriate because of limited space in the artery past the stenosis. The important point is that length of the imaging window section 106 is based upon the intended application.

The dilation section 107 of the catheter 100 of the present invention connects proximally with the imaging window section 106. It includes a balloon 104 that can be inflated or deflated by passing a fluid through a tube 105. The tube 105 is adjacent a length of flexible tube 109 which forms a passage for passing a guidewire or an ultrasound probe through the balloon 104. The distal and proximal ends of the balloon 104 connect sealingly with the tubes 105,109. The spaces shown in FIG. 1 between the balloon 104 and the tubes 105,109 are for clarity of presentation. As well known to those of skill in the art, balloon sizes are application dependent as with known dilation catheters. Radio opaque markers 102,103 are also included so that the location of the dilation section 107 can be determined. However, variations are possible; for example, in certain embodiments, the radio opaque markers 102,103 are placed just proximal and distal of the balloon 104 to delineate its length. In another alternate embodiment, the radio opaque markers 102,103 are replaced with a single marker (not shown) that locates the center of the balloon or some other known point within the dilation section 107.

Figure 1A:
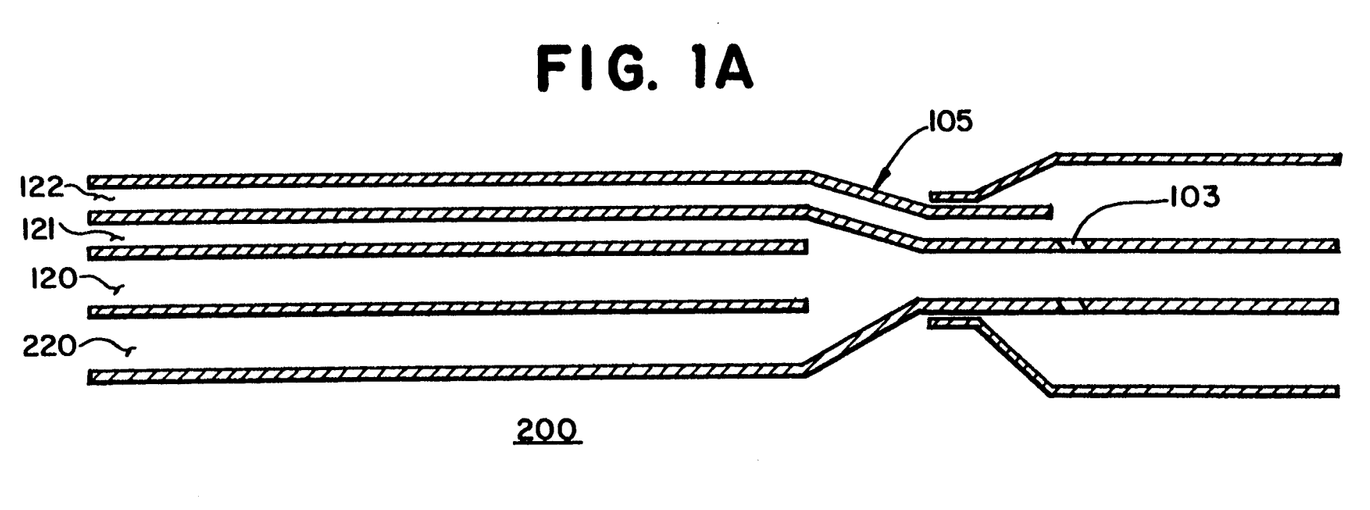
FIG. 1A is a longitudinal cross section, similar to FIG. 1, of a section of a catheter having a fourth lumen.
Figure 2:
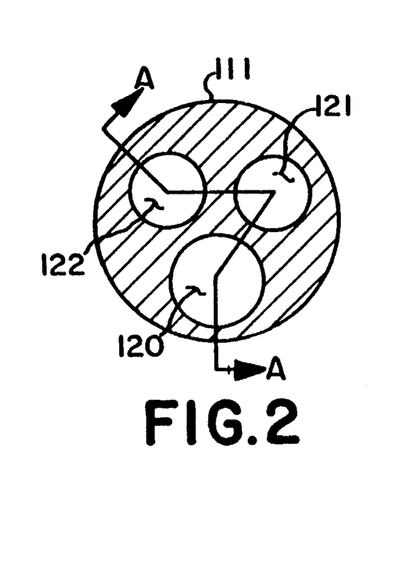
FIG. 2 is a cross-sectional view of a catheter made in accordance with the present invention, taken along line 2—2 in FIG. 1.

The cross-sectional arrows 2—2 shown in FIG. 1 indicate a location within the triple lumen section 111 of catheter 100. FIG. 2 illustrates this cross-section. The triple lumen section 111 is a tubular flexible elongate member containing at least three lumens 120,121,122. Preferably, a probe lumen 120 is sized to slidingly accept an ultrasound probe, a wire lumen 121 is sized to slidingly accept a guidewire, and an inflate/deflate lumen 122 is provided; the size of the latter affects the time required to inflate and deflate the balloon 104. However, as shown in FIG. 1A, a fourth lumen 220 is also provided in certain embodiments.

Figure 3:
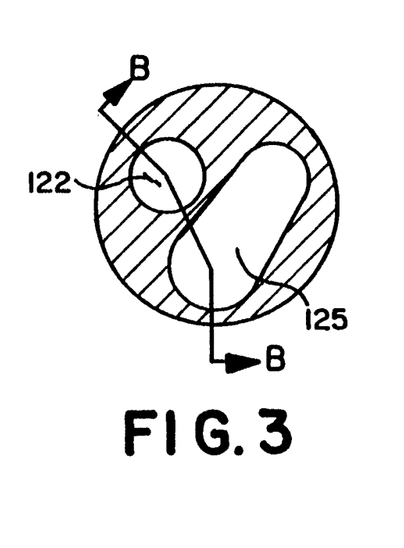
FIG. 3 is a cross-sectional view of a catheter made in accordance with the present invention, taken along line 3—3 in FIG. 1.
Figure 4:
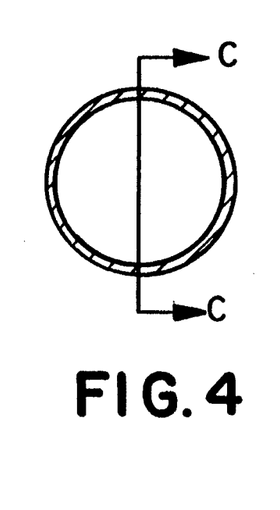
FIG. 4 is a cross-sectional view of a catheter made in accordance with the present invention, taken along line 4—4 in FIG. 1.

Referring still to FIG. 2, it should be emphasized that, in the region near arrows 2—2, FIG. 1 depicts a cross-sectional view of the catheter 100 taken along the irregular line A—A. This cross-section has been chosen in order to clarify the function of various lumens. Similarly, the cross-section of FIG. 1 shown near arrows 3—3 is depicted in FIG. 3, and this cross-section is obtained by sectioning as indicated by arrows B—B in FIG. 3. Finally, the cross-section of FIG. 1, shown near arrows 4—4, is obtained by sectioning as indicated by arrows C—C in FIG. 4.

Referring again to FIGS. 1-2, the length of the triple lumen section 111 of catheter 100 is application dependent; it extends proximally to nearly the proximal end of the catheter 100 (not illustrated) where appropriate fittings, adapters, connectors, valves and seals, all well known within the art, are added. In a catheter intended for PTCA, the triple lumen section 111 is preferably between about 100 cm (39.4 inches) to 150 cm (59.1 inches) in length. The probe lumen 120 and inflate/deflate lumen 122 extend essentially the complete length of the triple lumen section 111; the guidewire lumen 121 extends the complete length in certain preferred embodiments. In other preferred embodiments, the guidewire lumen 121 extends proximally from about the location of arrow 3—3 shown in FIG. 1 for a fraction of the triple lumen length. For instance, a 20-30 cm (7.9-11.8 inch) guidewire lumen 121 can be used for PTCA catheters. As used herein, the term "triple lumen length" refers to the longest of the three lumens, 120,121,122. For example, if the guidewire lumen 121 is 25 cm (9.8 inches) long and the probe lumen 120 and inflate/deflate lumen 122 are 120 cm (47.2 inches) long, then the catheter has a 120 cm (47.2 inch) long "triple lumen length."

Referring still to FIGS. 1-3, another embodiment of the guidewire lumen 121 extends the full length of the triple lumen section 111 except for a short interruption where the exterior wall is removed to expose the lumen 121. This embodiment allows a single catheter to be used as if the guidewire lumen 121 ran the full length of the triple lumen section 111 or as if the guidewire lumen 121 extends proximally from arrows 3—3 in FIG. 1 for a fraction of the triple lumen length.

A "transition" region in the vicinity of line 3—3 of FIG. 1 joins the guidewire lumen 121 and probe lumen 120 into a single merging lumen 125 which then extends distally through the balloon 104 and imaging window section 106. The merging lumen 125 of the transition region is most preferably constructed in accordance with invention disclosed in U.S. patent application Ser. No. 773,037 filed on Oct. 8, 1991 entitled "Ultrasonic Imaging Sheath" naming James M. Griffith as the inventor, the entirety of which is incorporated by reference as if fully set forth herein. As disclosed therein, a catheter is constructed with a distal lumen that terminates with a distal tip having a tip lumen sized to accept a guidewire. The distal lumen is connected to a dual lumen region having a probe lumen and a wire lumen by an intermediate section that advantageously permits the alternate acceptance of either the guidewire or the probe in the intermediate lumen. The construction details, methods of use and other advantages of the disclosed invention may be found in the referenced specification, which is incorporated herein in its entirety by reference thereto.

Thus, as shown in FIG. 1 the probe lumen 120 is directly connected to the merging lumen 125 and passes through the balloon 104, while the guidewire lumen 121 is offset. However, it will be understood that this is just one example of how the transition region can be offset from the lumen passing through the balloon 140. The transition region is smoothly tapered on its outside surface to make catheter 100 atraumatic to the patient lumen being imaged.

Figure 5:
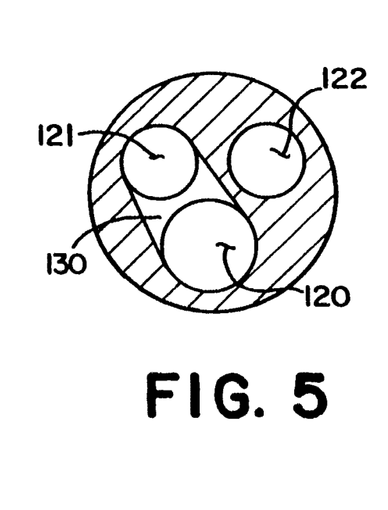
FIG. 5 is a cross-sectional view of a catheter made in accordance with the present invention, taken along line 5—5 in FIG. 1.
Figure 6:
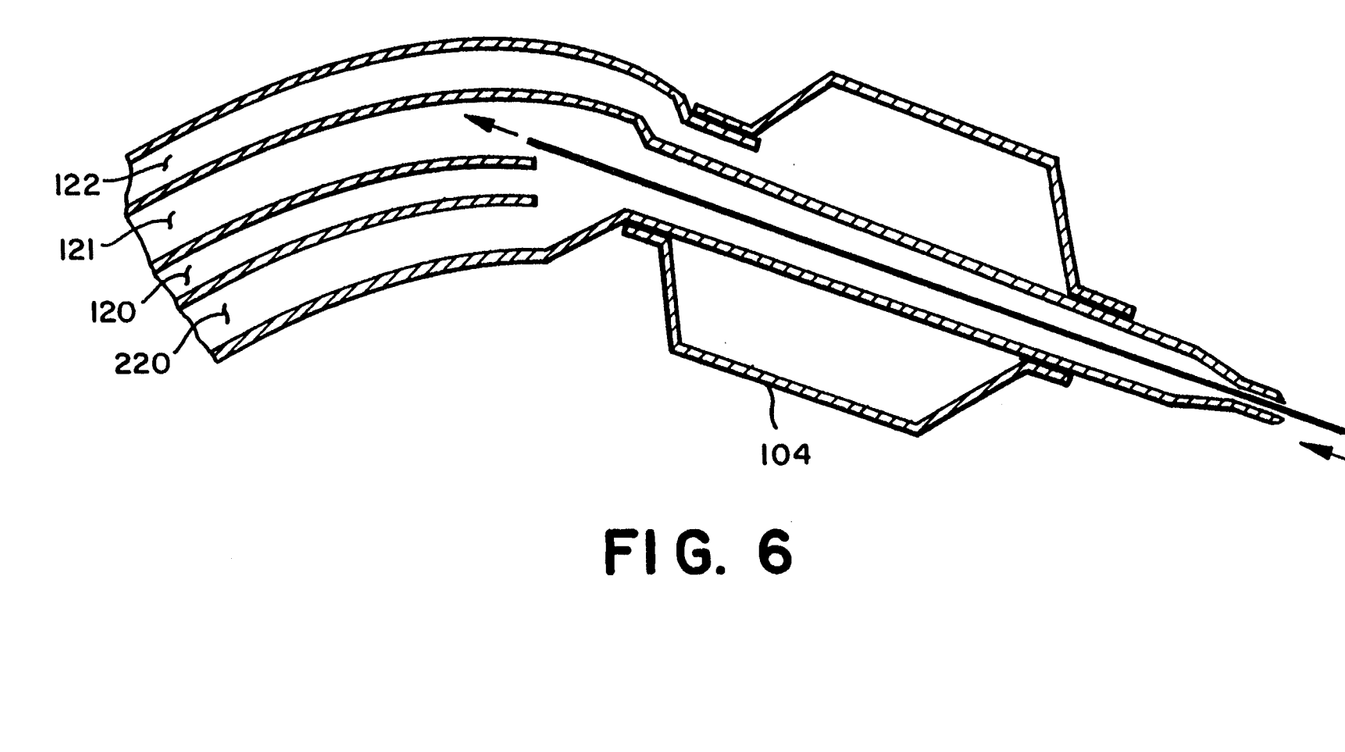
FIG. 6 is a cross-sectional view of a catheter made in accordance with the present invention that is being back loaded in accordance with certain aspects of the present invention.

Another aspect of the present invention is that the transition region contains a design feature which makes "back loading" a guidewire into a catheter very easy. As known in the art, back loading refers to the practice of threading the proximal end of a wire into the distal end of a catheter lumen and then moving the end of the wire through the wire lumen until it exits the proximal end of the catheter lumen. The catheter 100 of the present invention is easily "back loadable" but, as the wire goes through the transition region it might enter the probe lumen 120 rather than the guidewire lumen 121 unless some structure or procedure prevents this mistake. As shown in FIGS. 3 and 5, the present invention provides a design feature which simplifies such back loading into the guidewire lumen 121. The larger transition lumen 125 shown in FIG. 3 illustrates the guidewire lumen 121 and probe lumen 120 joining together in the transition lumen 125, as described above. This transition lumen 125 consists of large radius and small radius arcs joined by approximately straight lines, angled like the sides of a funnel; the larger arc portion aligns with a probe lumen wall, while the smaller arc aligns with a guidewire lumen wall. FIG. 5 illustrates a cross section of catheter 100 taken at arrows 5—5 in FIG. 1; the cross-section is taken at a location distal of where the wire lumen 121 and probe lumen 120 join. FIG. 5 shows the ridge 130 of catheter body material between the lumens 120,121, and also shows how the transition region lumen 125 aligns with the probe lumen 120 and wire lumen 121. The circumferential position of the guidewire lumen 121 is preferably visibly marked on catheter 100; the mark can be provided, for example, with a colored stripe (not shown) in the triple lumen region 111 or by the position and shape of a radio opaque marker 129.

Thus, in order to back load a guidewire into catheter 100 of the present invention: (1) insert the wire into the distal catheter tip, (2) bend the catheter so that the transition region resembles an arc with the guidewire lumen away from the center of curvature; and (3) push the wire proximally into the wire lumen 121. Since, in the absence of deflecting forces, the guidewire is basically straight, bending the catheter 100 causes the tip of the wire to drop into the narrow end of the above-described "funnel." The narrow end of the funnel aligns with the guidewire lumen 121 and hence, the guidewire passes into the guidewire lumen 121 when the wire moves proximally within the catheter 100. The funnel (and hence the transition region) preferably has a longitudinal length of about 1 cm (0.4 inches) so that a gentle curvature provides reliable back loading.

The preceding description of the transition region 125 is for the case where the probe lumen 120 is of larger diameter than the guidewire lumen 121. The description is modified if the probe lumen 120 and the guidewire lumen 121 are of equal diameter, or if the guidewire lumen 121 is larger than the probe lumen 120.

The position of the transition region 125 and hence the distal end of the wire lumen 121 and probe lumen 120, is designated or inferred in X-ray views from one or more radio opaque markers 129 placed as shown, in or near the transition region 125.

In the preceding description of back loading those of skill in the art will appreciate and understand that the guidewire and catheter movements are relative; a proximal guidewire movement is equivalent to a distal catheter movement.

It is also known in the art that changing catheters while leaving the guidewire in place using conventional "over-the-wire" PTCA catheters is difficult. A solution to this problem is the so-called "rapid exchange" catheter, wherein the guidewire lumen runs only for a fixed distance along the distal end of the catheter, e.g., a distal section about 0.8 feet (25 centimeters) long. Although these designs eliminate the need for crimping additional lengths of guidewire to the proximal end, the catheter may not "track" the guidewire as well as desired. A further improvement to the "rapid exchange catheter" is the so-called "convertible" catheter that includes an opening in the sidewall of a guidewire lumen; the opening permits the guidewire to be passed in either over-the-wire or rapid exchange fashion. The present invention may be adapted for use as either a "rapid exchange" catheter by shortening the proximal end of the guidewire lumen, or, alternatively, an opening can be provided in the sidewall to permit the catheter of the present invention to function as a "convertible" catheter.

The present invention also provides improved methods of performing balloon dilation and intraluminal ultrasonic imaging within a subject. For example, the catheter 100 of the present invention described above can be used for a PTCA procedure. An ultrasound probe is inserted into the probe lumen 120 with the distal tip of the probe proximal to the transition region 125. Doses of contrast media are supplied where needed to allow X-ray visualization and anatomic orientation. A guidewire is introduced through a guiding catheter and into the proper coronary artery. After the wire tip is positioned on the distal side of the restriction or lesion, the wire is used to guide the catheter 100 of the present invention into the coronary artery. The imaging window section 106 is placed across the stenosis using X-ray visualization, and the wire is retracted so that the distal tip of the wire resides in the wire lumen 121 and is proximal of the transition region 125. An ultrasound imaging probe is then advanced into the imaging window section 106 to obtain pre-dilation ultrasound images. Next, the probe is retracted into the probe lumen 120, the guidewire advanced distal of the catheter 100, and the catheter 100 is moved distally so that the balloon 104 crosses the lesion, and the balloon 104 is then inflated to dilate the lesion. After the balloon 104 is deflated, the catheter 100 is moved proximally until the imaging window section 106 is again across the lesion. Portions of the procedure are then repeated as necessary to obtain post-dilation ultrasound images. Although an "image/dilate/image" sequence is described above, it will be understood that other sequences are also useful. For instance, if post-dilation imaging revealed the need, a second dilation could be performed. Use of the present invention has been described in a PTCA application. It is understood, however, that the catheter 100 disclosed herein can also be used in other invasive procedures involving various body lumens.

Additionally, those of skill in the art will realize that a fourth lumen 220 could be incorporated proximal of the dilating section in the catheter 200 as illustrated in FIG. 1A and described above. As shown, the fourth lumen joins the lumen 120 and the lumen 121 in the vicinity of the cavity 105, it being understood that like reference numerals refer to the structure shown in and described with reference to FIG. 1. The location where the lumens 220,120,121 merge could be moved proximally. Alternatively, the fourth lumen 220 can be connected to the balloon lumen at a point distal of the connection point shown in FIG. 1A. The catheter 200 could then be used to deliver other devices, probes or sensors and the like, permitting other signals or substances to be introduced into the patient, other parameters monitored or other therapies initiated. Furthermore, those of ordinary skill will realize that the probe lumen 120 in the catheter 100 shown in FIG. 1 need not necessarily contain an ultrasound probe. The probe lumen 120 could be used to deliver other devices, probes or sensors and the like, permitting other signals or substances to be introduced into the patient, other parameters monitored or other therapies initiated.

In addition, those of ordinary skill will realized that while FIG. 1 shows the preferred location on the catheter to seal the proximal end of the balloon, other locations such as on the distal end of the triple lumen section can also be used.

Although the present invention has been described in what is presently considered the most practical and preferred embodiment it is to be understood that the invention is not to be limited to the disclosed embodiment. The invention is intended to cover the various modifications and equivalent arrangements included within the spirit and scope of the appended claims.

What is claimed is:

1. An imaging sheath comprising:
   a flexible dual lumen section comprising a guide wire lumen through which a guide wire passes, and a probe lumen through which a probe passes, wherein said lumens have proximal and distal ends; and
   a flexible intermediate section joined to the flexible dual lumen section at a communication point, the intermediate section comprising an intermediate lumen communicating with both the wire lumen and the probe lumen, wherein the intermediate lumen alternately receives the guide wire and the probe; and
   a radio opaque marker indicating the communication point of said dual lumen section and intermediate section.

2. The sheath of claim 1 further comprising:
   a flexible tapered distal tip portion through which the guide wire passes.

3. The sheath of claim 1 further comprising:
   a flexible tapered tip portion having a lumen sized to pass the guide wire, wherein said tip portion contains a radio opaque marker.

4. The sheath of claim 1 wherein the guide wire lumen is of a first diameter and the ultrasound probe lumen is of a smaller diameter.

5. The sheath of claim 1, wherein the probe is an ultrasound probe.

6. An ultrasound imaging sheath comprising:
   a dual lumen section comprising a guide wire lumen and an ultrasound probe lumen, wherein a cross-section of said dual lumen section and at least one of the lumens is circular; and
   an intermediate section connected to the dual lumen section and comprising an intermediate lumen communicating with both the wire lumen and the probe lumen sized to alternately pass a guide wire and an ultrasound probe.

* * * * *

UNITED STATES PATENT AND TRADEMARK OFFICE
CERTIFICATE OF CORRECTION

PATENT NO. : 5,400,789
DATED : March 28, 1995
INVENTOR(S) : James M. Griffith

It is certified that error appears in the above-indentified patent and that said Letters Patent is hereby corrected as shown below:

On the title page, item [54], and Column 1, line 2:
In the title, insert --and-- after the word "wire".

Signed and Sealed this

Twentieth Day of August, 1996

Attest:

BRUCE LEHMAN

Attesting Officer

Commissioner of Patents and Trademarks

Disclaimer 5,400,789 - James M. Griffith, Phoenix, Ariz. SHEATH FOR GUIDE WIRE PROBE. Patent dated March 28, 1995. Disclaimer filed May 3, 1999, by the assignee, Boston Scientific Corporation.
Hereby enters this disclaimer to all claims of said patent.
*(Official Gazette,* June 22, 1999)